United States Patent [19]

Verbrugge et al.

[11] 4,042,616

[45] Aug. 16, 1977

[54] PREPARATION OF CYCLOPROPANECARBOXYLATES

[75] Inventors: Pieter A. Verbrugge; Elisabeth W. Uurbanus, both of Amsterdam, Netherlands

[73] Assignee: Shell Oil Company, Houston, Tex.

[21] Appl. No.: 518,855

[22] Filed: Oct. 29, 1974

[30] Foreign Application Priority Data

Nov. 2, 1973 United Kingdom .............. 51005/73

[51] Int. Cl.² ............................................ C07C 67/30
[52] U.S. Cl. ................................. 260/468 G; 260/389; 260/468 H; 260/469
[58] Field of Search ........................ 260/468 H, 468 G

[56] References Cited

U.S. PATENT DOCUMENTS 3,823,177   7/1974   Fanta .............................. 260/468 G

FOREIGN PATENT DOCUMENTS 7,205,298   10/1972   Netherlands
7,212,973   3/1973    Netherlands
7,306,662   11/1973   Netherlands
1,243,858   8/1971    United Kingdom

OTHER PUBLICATIONS

Allinger, *Organic Chemistry*, p. 425, (1971).
Matsui, *Chem. Abst.*, 68:39156j (1968).
Konzelman, *Chem. Abst.* 69:105990a, (1968).
Meshcheryakov, *Chem. Abst.* 54:24436d.
Lukina *Chem. Abst.* 72:132113k.
Conia, *Accounts of Chemical Research*, 5 pp. 33–40 (1972).

*Primary Examiner*—Lorraine A. Weinberger
*Assistant Examiner*—Michael Shippen

[57] ABSTRACT

Preparation of tert-(cyclo)alkyl 1-hydrogen-2-hydrocarbylcyclopropanecarboxylates or 1-tert-(cyclo)alkyl spiro [2,p] alkanecarboxylates where $p$ is an integer of at least 2 by reaction of a tert-(cyclo)alkyl 1-hydrogen-2-halocyclopropanecarboxylate with a (1) hydrocarbylmagnesium halide or (2) polymethylene-bis(-magnesium halide)- or a magnesiacycloalkane, followed by addition of a proton donor to the reaction product thus obtained.

10 Claims, No Drawings

PREPARATION OF CYCLOPROPANECARBOXYLATES

BACKGROUND OF THE INVENTION

1. Field of the Invention

The invention relates to a process for the preparation of tert-(cyclo ) alkyl 1-hydrogen-2-hydrocarbylcyclopropanecarboxylates or 1-tert- (cyclo)alkyl spiro[2,$p$]-alkanecarboxylates, $p$ representing an integer of at least 2.

2. Description of the Prior Art 2,2-Dihalocyclopropanecarboxylates and certain derivatives thereof - as stated in the Netherlands Pat. application Nos. 7,205,298 and 7,212,973 - are biologically active, exhibiting in particular fungicidal and pesticidal properties. The fungicidal activity is especially marked against rice blast (Pyricularia oryzae). The pesticidal activity is whown by certain of the compounds against a wide range of insect and acarid pests.

Certain 2,2,3,3-tetraalkylcyclopropanecarboxylates - as stated in British Pat. specification No. 1,243,858, are also biologically active, combining a high insecticidal activity with low mammalian toxicity.

2,2-Dihalocyclopropanecarboxylic acids, from which the above-mentioned- 2,2-dihalocyclopropanecarboxylates are derived, may easily be prepared from simple precursors. This can be explained as follows for the preparation of 2,2-dichloro-3,3-dimethylcyclopropanecarboxylic acid. 2-Methyl-2-pentene-4-one (mesityl oxide) is converted by means of the haloform reaction into potassium 3-methylcrotonate, which in turn is converted into the corresponding tert-butyl ester. Then, dichloromethylene generated in situ is added to this ester according to Netherlands patent application 7306662 to form tert-butyl 2,2-dichloro-3,3-dimethylcyclopropanecarboxylate, from which the corresponding acid can be prepared.

The 2,2,3,3-tetraalkylcyclopropanecarboxylic acid from which the above-mentioned 2,2,3,3-tetraalkylcyclopropanecarboxylates are derived can be prepared by (a) reaction of alkenes with a diazoacetic ester in the presence of a cupric sulphate catalyst, as described in *Chemical Abstracts* 54,24436 d, followed by liberation of the acid from the ester obtained, or (b) base-indused skeletal rearrangement of alpha-halogenated cyclobutanones, as described by J. M. Conia in *Accounts of Chemical Research* 5 (1972) 33–40, or (c) addition of a Grignard reagent to the double bond of cyclopropene hydrocarbons, as described in *Chemical Abstracts* 72, 132113 K, followed by reaction of the addition compound with dry ice and acidification.

The above shows that the 2,2,3,3-tetramethylcyclopropanecarboxylates are considerably more difficult to prepare than the 2,2-dihalocyclopropanecarboxylates. It would therefore be very attractive if there were a process for the replacement of the two halogen atoms in the 2,2-di-halocyclopropanecarboxylates by two alkyl groups. The present invention provides such a process.

SUMMARY OF THE INVENTION

The present invention is directed to a process for converting tert-(cyclo)alkyl 1-hydrogen-2-halocyclopropanecarboxylates into tert-(cyclo)alkyl 1-hydrogen-2-hydrocarbylcyclopropanecarboxylates or 1-tert-(cyclo)alkyl spiro[2,$p$]alkanecarboxylates in high yields by a very selective process.

DESCRIPTION OF THE PREFERRED EMBODIMENT

In accordance with the present invention there has been found a process for the production of tert-(cyclo)alkyl 1-hydrogen-2-hydrocarbylcyclopropanecarboxylates or 1-tert-(cyclo)alkyl spiro[2,$p$]alkanecarboxylates, $p$ representing an integer of at least 2, in which process a tert-(cyclo)alkyl 1-hydrogen-2-halocyclopropanecarboxylate — of which the halogen atom(s) has (have) an atomic number of at least 17 — is caused to react in solution with a (1) hydrocarbylmagnesium halide of which the halogen atom has an atomic number of at least 17, or with a dihydrocarbylmagnesium, or (2) polymethylene-bis(magnesium halide) — of which the halogen atoms have an atomic number of at least 17 and which contains $p$ methylene groups per molecule — or a magnesiacycloalkane having $p$ carbon atoms per cycloalkane nucleus, respectively, and a proton donor is added to the reaction product thus obtained.

The novel process according to the present invention — hereinafter named the novel process — may be performed in a very simple way by stirring a solution containing the above-stated reactants for a certain period. The tert-(cyclo)alkyl 1-hydrogen-2-hydrocarbylcyclopropanecarboxylates are usually obtained in a very high yield, which may be 90–96%, calculated on the starting carboxylate, and may be conceived to be formed by replacement of the halogen atom on the 2-position of the starting carboxylate by the hydrocarbyl group of the hydrocarbylmagnesium halide or the dihydrocarbylmagnesium. The use of tert-(cyclo)alkyl 1-hydrogen-2-halocyclopropanecarboxylates with two, three or four halogen atoms is within the scope of the invention; all halogen atoms are replaced in this case by hydrocarbyl groups.

The novel process applies to those 1-hydrogen-2-halocyclopropanecarboxylates which are tert-(cyclo)alkyl esters; the halogen atom(s) on the 2-position of the cyclopropane ring is (are) not replaced by hydrocarbyl groups when the novel process is modified by applying a 1-hydrogen-2-halocyclopropanecarboxamide - whether or not with a substituted NH$_2$ group -, a sec (cycloalkyl or primary alkyl 1-hydrogen-2-hydrocarbylcyclopropanecarboxylate instead of a tert-(cyclo)alkkyl 1-hydrogen-2-hydrogen carbylcyclopropanecarboxylate as a starting material. The novel process only applies to those tert-(cyclo)alkyl 2-halocyclopropanecarboxylates which have a hydrogen atom on the 1-position of the ring, because the halogen atom(s) on the 2-position of the cyclopropane ring is (are) likewise not replaced by hydrocarbyl groups when the novel process is modified by using a 1-hydrocarbyl-2-halocyclopropanecarboxylate instead of a 1-hydrogen-2-halocyclopropanecarboxylate as a starting material.

The starting tert-(cyclo)alkyl carboxylates may, for example, be tert-butyl, 2-methyl-2-butyl, 2-methyl-2-pentyl, 3-methyl-3-pentyl, 3-methyl-3-hexyl, methylcyclohexyl, ethylcyclohexyl, methylcylotyl and bridged hydrocarbyl, such as adamantyl, bicyclo[1.1.0]butyl and bicyclo[3.2.1] octyl carboxylates. Very good result are usually obtained with tertalkyl carboxylates, particularly with tert-butyl carboxylates.

The starting tert-(cyclo)alkyl 1-hydrogen-2-halocyclopropanecarboxylate may have one, two, three or four halogen atoms attached to the cyclopropane ring. Possible starting compounds are 2,2-dihalocyclopropanecarboxylates, 2,3-dihalocyclopropanecarboxylates, 2,3,3-trihalocyclopropanecarboxylates and 2,2,3,3-tetrahalocyclopropanecarboxylates. Very good results are obtained when the tert-(cyclo)alkyl 1-hydrogen-2-halocyclopropanecarboxylate is a 2,2-dihalocyclopropanecarboxylate The halogen atoms in the starting tert-(cyclo)alkyl 1-hydrogen-2-halocyclopropanecarboxylates may be chlorine, bromine or iodine atoms; when two, three or four halogen atoms are present, they may be the same or different, the possibilities for two halogen atoms being as follows: two chlorine atoms, two bromine atoms, two iodine atoms, a chlorine and a bromine atom,, a chlorine and an iodine atom or a bromine and an iodine atom. All of these combinations usually give very high yields of tert-(cyclo)alkyl 1-hydrogen-2-hydrocarbylcyclopropanecarboxylates. As the use of chlorine compounds offers cost advantages over that of the corresponding bromine and iodine compounds, tert-(cyclo)alkyl 1-hydrogen-2-chlorocyclopropane-carboxylates will be preferred.

The starting hydrocarbylmagnesium halide may be a chloride, bromide or iodide. All of these halides usually give very high yields of tert-(cyclo)alkyl 1-hydrogen-2-hydrocarbylcyclopropane-carboxylates. In view of the above-mentioned cost advantages, hydrocarbylmagnesium chlorides are preferred.

The hydrocarbyl group in the hydrocarbylmagnesium halide, the two hydrocarbyl groups in the starting dihydrocarbylmagnesium and any hydrocarbyl groups on the 2- and 3-positions on the cyclopropane ring of the starting carboxylate which are not occupied by halogen atoms may, for example, be an alkyl, alkenyl, cycloalkyl or aryl group. Very good results are usually obtained when these hydrocarbyl groups are alkyl groups. The alkyl groups may be straight or branched and may contain up to, say, 20 carbon atoms. Examples of alkyl groups which may be used are methyl, ethyl, propyl, i-propyl, butyl, sec-butyl, tert-butyl and pentyl groups; examples of hydrocarbyl-substituted alkyl groups are benzyl, phenetyl and trityl groups; examples of aryl groups are phenyl and naphthyl groups and examples of hydrocarbyl-substituted aryl groups are tolyl and xylyl groups. Among the alkyl groups, methyl and ethyl groups, particularly methyl groups, usually afford very good results.

The reaction mixture formed by the reaction of the starting carboxylate with the starting magnesium compound is provided with a proton donor to set free the tert-(cyclo)alkyl 1-hydrogen-2hydrocarbylcyclopropanecarboxylate. Examples of proton donors are water, alkanols and alkanecarboxylic acides. Water is very suitable. The addition of pure water causes a basic magnesium salt to precipitate, whereas precipitation of a basic magnesium salt is avoided when the water contains an acid, such as sulphuric, hydrochloric or acetic acid, or a compound which forms water-soluble complexes with magnesium salts, such as ammonium chloride.

The two hydrocarbyl groups in the starting dihydrocarbylmagnesium may be the same or different. The novel process may be performed starting from pure dihydrocarbylmagnesium compounds, but these compounds are difficult to obtain. Dihydrocarbylmagnesium compounds will usually be present when hydrocarbylmagnesium halides are used as starting compounds, because in solution hydrocarbylmagnesium halides are usually in equilibrium with dihydrocarbylmagnesium compounds and a magnesium halide.

It is possible to start from two or more different tert-(cyclo)-alkyl 1-hydrogen-2-halocyclopropanecarboxylates, hydrocarbylmagnesium halides, dihydrocarbylmagnesiums, polymethylenebis(magnesium halides) and/or magnesiacycloalkanes. In this case two or more different tert-(cyclo)alkyl 1-hydrogen-2-hydrocarbylcopropanecarboxylates or 1-tert-(cyclo)alkyl spiro[2,p]alkanecarboxylates will usually be formed. For example, when a mixture of two hydrocarbylmagnesium halides having different hydrocarbyl groups react with a tert-(cyclo)alkyl 1-hydrogen-2,2-dihalocyclopropanecarboxylate, three different tert-(cyclo)alkyl 1-hydrogen-2-hydrocarbylcyclopropanecarboxylatesare usually formed, namely one with the same hydrocarbyl groups, originating from one of the hydrocarbylmagnesium halides, the second with the same hydrocarbyl groups, originating from the other hydrocarbylmagnesium halide and the third with different hydrocarbyl groups, one originating from and and one from the other hydrocarbylmagnesium halide.

The solymethylenebis(magnesium halides), which may also named α,ω-bis(halomagnesio)alkanes, and the magnesiacycloalkanes react according to the invention with formation of 1-tert(cyclo)alkyl spiro[2,p]alkanecarboxylates, p being an integer of at least 2. The polymethylenebis(magnesium halides) are usually in solution in equilibrium with a mixture of magnesiacycloalkanes and magnesium halide. The spiro compounds formed are monospiro compounds of which the carbon atom forming the spiro union has been the carbon atom on the 2-position in the tert-(cyclo)alkyl 1-hydrogen-2-halocyclopropanecarboxylate. The polymethylene group and the magnesiacycloalkanes may, for example, have less than 10 methylene groups and be a di-, tri-, tetra-, penta-, hexa-, hepta- or octamethylene group; from the compounds with these groups spiro[2,2], [2,3], [2,4], [2,5], [2,6], [2,7]or [2,8]alkanecarboxylates, respectively, are formed. The spiro compounds formed are usually accompanied by minor amounts of by-products, inter alia of tert-(cyclo)alkyl 1-hydrogen-2-alkylcyclopropanecarboxylates of which the alkyl groups have p carbon atoms per group.

The halogen atoms in the polymethylenebis(magnesium halide) may be the same or different, i.e. two chlorine atoms, two bromine atoms, two iodine atoms, a chlorine and a bromine atom, a chlorine and an iodine atom or a bromine and an iodine atom. As the use of chlorines compounds offers cost advantages over that of the corresponding bromine and iodine compounds, two chlorine atoms are preferred.

Those 2- and 3-positions on the cyclopropane ring of the starting carboxylate which are not occupied by halogen atoms may be occupied by hydrogen atoms and/or hydrocarbyl groups, in any combination. These hydrocarbyl groups may be the same or different and, when three hydrocarbyl groups are present, only two may be the same.

It is not precluded that (a) the hydrocarbyl groups of the hydrocarbylmagnesium halide, of the dihydrocarbylmagnesium and —when present —those on the 2- and 3-positions of the starting tert-(cyclo)alkyl 1-hydrogen-2-halocyclopropanecarboxylate, and (b) the polymethylene group in the polymethylenebis(magnesium halide) and the magnesiacycloalkane carry one or more substituents. Examples of possible substituents are alkoxy, alkylthio and silyl groups and fluorine atoms.

Examples of very suitable starting carboxylates are tert-butyl 2,2-dichlorocylopropanecarboxylate, tert-butyl 2,2-dichloro-3-methylcyclopropane carboxylate, tert-butyl 2,2-dichloro-3,3-dimethylcylopropanecarboxylate, tert-butyl 2,2-dichloro-3-methyl-3-ethylcyclopropanecarboxylate, tert-butyl 2,2-dichloro-3,3-diethylcyclopropanecarboxylate and tert-butyl 2,2-dichloro-3,3-di-n-propylcyclopropanecarboxylate. Excellent results have been obtained with tert-butyl 2,2-dichloro-3,3-dimethylcyclopropanecarboxylate and tert-butyl 2,2-dichloro-3,3-diethylcyclopropanecarboxylate.

Examples of very suitable starting hydrocarbylmagnesium halides are methylmagesium iodide, ethylmagnesium iodide, 2-methylpropylmagnesium chloride, 2-methylpropylmagnesium bromide and particularly methylmagnesium chloride and ethylmagnesium chloride.

The starting hydrocarbylmagnesium halides are so-called Grignard compounds whose preparation is described in the literature. In most cases they are simply prepared by reaction magnesium with a hydrocarby halide dissolved in a suitable solvent. The preparation of the hydrocarbylmagnesium halide may be performed in the presence or the absence of the starting tert-(cyclo)alkyl 1-hydrogen-2-halocyclopropanecarboxylate; the yield of the tert-(cyclo)alkyl 1-hydrogen-2-hydrogcarbylcyclopropanecarboxylate is usually highest in the latter case, by-products being formed in the former case.

The novel process may be performed in solvents which are suitable for Grignard reactions. Ethers are usually very suitable, for example diethyl ether, di-n-butyl ether, diisopentyl ether, anisole, ethyl and dibutyl ethers of ethylene glycol, diphenyl ether, tetrahydrofuran, 2-methyltetrahydrofuran, tetrahydropyran, 4-methyl-1,3-dioxane, dihydropyran, tetrahydrofurfuryl ethyl ether and 2-ethoxytetrahydrofuran. The use of solvents other than ethers is not precluded, for example of (cyclo)aliphatic and aromatic hydrocarbons or of heterocyclic compounds. Tetrahydrofuran is an example of a suitable heterocyclic compound.

The molar ratio in which the tert-(cyclo)alkyl 1-hydrogen-2- halocyclopropanecarboxylate and the hydrocarbylmagnesium halide are employed and the temperature of the solution are not critical and may vary within wide ranges. The molar ratio carboxylate/halide to be used in a particular case can easily be determined by simple experiments. This molar ratio is about 3 when tert-butyl 2,2-dimethyl-3,3-dichlorocyclopropanecarboxylate is reacted with methylmagnesium chloride. The temperature of the solution will usually lie between 0° and 100° C and in particular between 15° and 40° C.

The tert-(cyclo)alkyl 1-hydrogen-2-hydrocarbylcyclopropanecarboxylate and 1-tert(cyclo)alkyl spiro[2,$p$]alkanecarboxylates may be isolated in a simple manner. For example, the reaction mixture is provided with dilute acide, the organic and aqueous phases formed are separated, the organic layer is washed with water and with a sodium bicarbonate solution until neutral, the washed organic liquid is dried and the dried liquid boiled down.

Tert-alkyl 1-hydrogen-2-hydrocarbylcyclopropanecarboxylates and 1-tert-alkyl spiro[2,$p$]alkanecarboxylates are novel compounds. The former group of novel compounds includes the tert-alkyl 1-hydrogen-2,2-dihydrocarbylcyclopropanecarboxylates, for example the tert-alkyl 1-hydrogen 2,2,3,3-tetrahydrocarbylcyclopropanecarboxylates and the latter the 1-tert-alkyl 2,2-dihydrocarbylspiro[2,$p$]alkanecarboxylates, for example the 1-tert-alkyl 2,2-dialkylspiro[2,$p$]-alkanecarboxylates. The tert-alkyl group in each of the two groups of novel compounds may, for example, be a tert-butyl group and the hydrocarbyl groups may, for example, be methyl groups.

The compounds prepared using the novel process are valuable intermediates for the preparation of pesticidally active 2,2,3,3-tetramethylcyclopropanecarboxylates by replacing the tert-butyl substituent with a wide variety of substituents which result in pesticidally active compounds, such as those disclosed in BritishPat. No. 1,243,858.

The invention is further illustrated by means of the Examples.

EXAMPLE 1

An amount of 0.04 gram atom (gat) magnesium and 0.04 mol methyl iodide was added to 10 ml diethyl ether and the mixture thus formed was kept boiling under a water-cooled reflux condenser until the magnesium had disappeared. Then, the mixture was cooled to 25° C and 0.01 mol tert-butyl 2,2-dichloro-3,3-dimethylcyclopropanecarboxylate was added. This addition caused the temperature to rise to 33° C. After 3 hours'stirring the excess Grignard compound was decomposed by dropwise addition of 5ml water. The tert-butyl 2,2,3,3-tetramethylcyclopropanecarboxylate simultaneously set free by the water addition was isolated by, consecutively acidifying with 0.1N aqueous hydrochloric acid until the solution was clear, separating the organic layer from the aqueous layer, washing the organic layer with water and with an aqueous sodium bicarbonate solution until the organic layer was neutral and drying the organic layer by contacting with solid potassium carbonate. The dried liquid was boiled down in a rotation evaporator until the pressure has been reduced to 0.016 bar abs. at a bath temperature of 40° C. The residue thus obtained consisted of pure tert-butyl 2,2,3,3-tetramethylcyclopropanecarboxylate, and its yield was 86%, calculated on tert-butyl 2,2-dichloro-3,3-di-methylcyclopropanecarboxylate.

EXAMPLE II

After 20 ml diethyl ether containing 0.02 gat magnesium had been cooled in an ice bath the cooled ether was saturated with gaseous methyl chloride under a water-cooled reflux condenser. Then, the ice bath was removed and the mixture allowed to adopt ambient temperature. After the start of the reaction between methyl chloride and magnesium, gaseous methyl chloride was again introduced into the mixture until the magnesium had been disappeared. Then, 0.005 mol tert-butyl 3,3-dichloro-2,2-dimethylcyclopropanecarboxylate was added to the mixture which caused the temperature to rise from 25° to 33° C. After three hours' stirring the excess Grignard compound was decomposed by dropwise addition of 0.1 N aqueous hydrochloric acid. The tert-butyl 2,2,3,3-tetramethylcyclopropanecarboxylate thus formed was isolated from the reaction mixture in the manner described in Example I. The yield of the latter carboxylate was 76%, calculated on tert-butyl 3,3-dichloro-2,2-dimethylcyclopropanecarboxylate.

EXAMPLE III

The experiment described in Example II was repeated but an amount of 0.015 gat magnesium instead of 0.02 gat was used. The yield of tert-butyl 2,2,3,3-tetramethylcyclopropanecarboxylate was 96%, calculated on starting carboxylate.

EXAMPLE IV

The experiment described in Example II was repeated but an amount of 0.01 gat magnesium instead of 0.02 gat was used and the mixture was stirred for an additional 12 hours before the magnesium compound formed was decomposed. The product obtained in the rotation evaporator consisted of equal quantities by weight of the starting ester and tert-butyl 2,2,3,3-tetramethylcyclopropanecarboxylate. The yield of the latter carboxylate was 50%, calculated on the starting carboxylate.

EXAMPLE V

In a round-bottom flask of one litre capacity placed in an oil bath an amount of 0.41 gat magnesium was heated for one hour in a nitrogen stream at a temperature of 200° C. Then, the flask was cooled to a temperature of 22° C and 200 ml diethyl ether was added. The flask was connected to a reflux condenser cooled with a mixture of solid carbon dioxide and isopropanol. A small iodine crystal was added to the flask and gaseous methyl chloride was conducted through the liquid in the flask. This introduction of methyl chloride caused the temperature of the liquid to rise from 22° to 26.5° C, but when methyl chloride started refluxing, the temperature slowly dropped. The introduction of methyl chloride was stopped when the temperature of the liquid had reached 5° c. Stirring was continued and the magnesium had disappeared 12 hours after the introduction of methyl chloride had been stopped. Then, 0.1 mol tert-butyl 2,2-dichloro-3,3-dimethylcyclopropanecarboxylate was added, which addition caused the temperature to rise from 22°to 36.5° C. Stirring was continued until the temperature had dropped to 22° C and the excess of Grignard compound had been decomposed by dropwise addition of water at this temperature. After addition of 200 ml n-pentane to the mixture thus formed, the tert-butyl 2,2,3,3-tetramethylcyclopropanecarboxylate set free by the water addition was isolated from the reaction mixture as described in Example I. The yield of the latter carboxylate was 91.5%, calculated on tert-butyl 2,2-dichloro-3,3-dimethylcyclopropanecarboxylate.

EXAMPLE VI

The experiment described in Example I was repeated with the only difference that 0.03 gat magnesium, 0.03 mol methyl iodide and 0.01 mol tert-butyl 3,3-diethyl-2,2-dichlorocyclopropanecarboxylate were used instead of 0.04 gat magnesium, 0.04 mol methyl iodide and 0.01 mol tert-butyl 2,2-dichloro-3,3-dimethylcyclopropanecarboxylate, respectively. The residue formed in the rotation evaporator consisted of tert-butyl 3,3-diethyl-2,2-dimethylcyclopropranecarboxylate. This compound was obtained in a yield of 80%.

EXAMPLE VII

The experiment described in Example I was repeated with the only difference that 0.03 gat magnesium and 0.03 mol ethyl iodide were used instead of 0.04 gat magnesium and 0.04 mol methyl idodie. The residue formed in tehe rotation evaporator consisted of tert-butyl 3,3-diethyl-2,2-dimethylcyclopropanecarboxylate. This compound was obtained in a yield of 60%.

EXAMPLE VIII

A mixture of 0.032 mol methyl iodide and 0.01 mol tert-butyl 2,2-dichloro-3,3-dimethylcyclopropanecarboxylate was added to 20 ml diethyl ether in which 0.04 gat magnesium was present. This addition causes the temperature to rise from 25° to 37° C and the liquid to boil. A water-cooled reflux condenser was present above the boiling liquid and the mixture was stirred for a period of six hours. The conversions of the carboxylate were 71.5, 90.7 and 100% after 2, 4 and 6 hours' stirring, respectively.

After 6 hours' stirring 20 ml n-pentane was added to the liquid and the reaction mixture was worked up as described in Example I. The product obtained in the rotation evaporator contained tert-butyl 2,2,3,3-tetramethylcyclopropanecarboxylate (yield 25%) and consisted of more than 50% by weight of compounds other than this carboxylate. The aqueous sodium bicarbonate solution which had been used for washing the organic layer in the working-up procedure contained 0.0027 mol sodium 2,2-dichloro-3,3-dimethylcyclopropanecarboxylate, being 27% of the starting carboxylate.

EXAMPLE IX

The experiment described in Example I was four times repeated using the four hydrocarbyl halides mentioned in Table I instead of methyl iodide. Table I states which compounds were found in the rotation evaporator.

Table I

| Exp. | starting halide | compounds formed |
|---|---|---|
| 1 | 1-bromo-2-methyl-propane | tert-butyl 2,2-dimethyl-3,3-(2-methyl-propyl)cyclopropanecarboxylate. |
| 2 | 1-bromo-2-methyl-1-propene | tert-butyl 2,2-dimethyl 3,3-(2-methyl-1-propenyl)cyclopropanecarboxylate; starting carboxylate and polymers |
| 3 | 1,4-dibromobutane') | 1-tert-butyl 2,2-dimethylspiro[2,4]-heptanecarboxylate and side products |
| 4 | 1,5-dibromopentane') | 1-tert-butyl 2,2-dimethylspiro[2,5]-octanecarboxylate and side products. |

') In this case the molar ratio halide:starting carboxylate was 2 instead of 4.

EXAMPLE X

After 200 ml diethyl ether containing 0.3 gat magnesium had been cooled in an ice bath the cooled ether was saturated with gaseous methyl chloride under a reflux condeser cooled with a mixture of acetone and solid carbon dioxide. Then, the ice bath was removed and the mixture allowed to adopt ambient temperature. After the start of the reaction between methyl chloride and magnesium, gaseous methyl chloride was again introduced into the mixture until the magnesium had been disappeared. Then, 0.1 mole tert-butyl 3,3-dichloro-2,2-dimethylcyclopropanecarboxylate was added to the mixture. After three hours' stirring 120 ml diethyl ether was distilled off and 200 ml n-pentane was added to the residue thus obtained. Subsequently, the excess Grignard compound was decomposed by dropwise addition of 0.1N aqueous hydrochloric acid. The tert-butyl 2,2,3,3-tetramethylcyclopropanecarboxylate simultaneously formed was isolated from the reaction mixture in the manner described in Example I. The organic layer which separated from the aqueous layer, was not contaminated with magnesium chloride, the latter compound being insoluble in n-pentane. The yield of the latter carboxylate was 96%, calculated on tert-butyl 2,2-dichloro-3,3-dimethylcyclopropanecarboxylate.

The experiment described in this Example was modified by applying 0.25 gat instead of 0.3 gat magnesium. The yield of tert-butyl 2,2,3,3-tetramethylcyclopropanecarboxylate was again 96%, calculated on tert-butyl 2,2-dichloro-3,3-dimethylcyclopropanecarboxylate.

EXAMPLE XI (for comparison)

Example I was repeated with the only difference that tert-butyl 1,3-dimethyl-2,2-dichlorocyclopropanecarboxylate was used instead of tert-butyl 2,2-dichloro-3,3-dimethylcyclopropanecarboxylate. This carboxylate, however, was recovered unchanged in the rotation evaporator.

Example I was again repeated with the only difference that N-tert-butyl 2,2-dichloro-3,3-dimethylcyclopropanecarboxamide was used instead of tert-butyl 2,2-dichloro-3,3-dimethylcyclopropanecarboxylate. This carboxamide, however, was recovered unchanged in the rotation evaporator.

Example I was repeated once more with the only difference that ethyl 2,2-dichloro-3,3-dimethylcyclopropanecarboxylate instead of tert-butyl 2,2-dichloro-3,3-dimethylcyclopropanecarboxylate was used. This ethyl ester was fully converted into 2,2-dichloro-1-(1-hydroxy-1-methylethyl)-3,3-dimethylcyclopropane.

It is well known that hydrocarbylmagnesium halides react with alkyl or allyl halides according to the equation

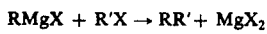

It is also known that hydrocarbylmagnesium halides react with carbonyl compounds, including esters, to produce alcohols:

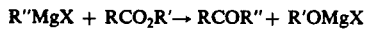

In attempting to prepare tert-(cyclo)alkyl-1-hydrogen-2-hydrocarbylcyclopropropane carboxylates or 1-tert-(cyclo)alkyl[2,p]alkanecarboxylates from tert-(cyclo)alkyl 1-hydrogen-2-halocyclopropane carboxylates, two points are available on the carboxylate for attack by the hydrocarbylmagnesium halide: (1) the halogen and (2) the carboxyl group.

Surprisingly, in the above reaction of tert-(cyclo)alkyl-1-hydrogen-2-halo-cyclopropanecarboxylates with hydrocarbylmagnesium halides the actual point of attack is essentially exclusively the halogen substituent on the cyclopropane ring. Thus, tert-(cyclo)alkyl esters are produced rather than tert-alcohols.

Similar reactions conducted with ethyl esters produced 2-halo-1-(1-hydroxymethylethyl)-3,3-dimethylcyclopropane. When such reactions were conducted with N-tert-butyl amide, only the starting amide was recovered. Reactions using tert-alkyl 1-hydrocarbon-2-halocyclopropanecarboxylate as the starting material resulted in unchanged starting material. These reactions were demonstrated in Example XI.

Thus the present novel process is characterized by a high selectivity to the tert-(cyclo)alkyl-1-hydrogen-2-halocyclopropane reactants and produces the desired tert-alkyl-1-hydrogen-2-hydrocarbylcyclopropane carboxylates and 1-tert-alkyl[2,p]alkanecarboxylates products in high yields without the aid of catalysts.

We claim as our invention:

1. A process or the production of a tertalkyl 1-hydrogen-2-alkylcyclopropanecarboxylate in which process (A) a tert-alkyl 1-hydrogen-2-halocyclopropanecarboxylate in which the halogen atom(s) has (have) an atomic number of at least 17 and the tert-alkyl group is a tert-alkyl group of from 4 to 7 carbon atoms or a tert-cycloalkyl group of from 7 to 9 carbon atoms, is contacted in solution with an alkylmagnesium halide in which the halogen atom has an atomic number of at least 17, or with a dialkylmagnesium, in which each of said alkyl groups contains up to 20 carbon atoms and (B) adding a proton donor to the reaction product thus produced.

2. A process as claimed in claim 1, in which a tert-alkyl 1-hydrogen-2,2-dihalocyclopropanecarboxylate is applied as the tert-alkyl 1-hydrogen-2-halocyclopropanecarboxylate.

3. A process as claimed in claim 1, in which an alkylmagnesium halide with not more than two carbon atoms per molecule is applied.

4. A process as claimed in claim 1, in which water is applied as the proton donor.

5. A process as claimed in claim 1, in which the tert-alkyl 1-hydrogen-2-halocyclopropanecarboxylate has two alkyl substituents on the 3-position of the cyclopropane ring.

6. A process as claimed in claim 5, in which tert-butyl 2,2-dichloro-3,3-dimethylcyclopropanecarboxylate is applied as the starting carboxylate.

7. A process as claimed in claim 5, in which tert-butyl 2,2-dichloro3,3-diethylcyclopropanecarboxylate is applied as the starting carboxylate.

8. A process as claimed in claim 3, in which methylmagnesium chloride is applied as the alkylmagnesium halide.

9. A process for the production of a 1-tert-alkyl spiro[2,4alkanecarboxylate in which process a tert-alkyl 1-hydrogen-2-halocyclopropanecarboxylate in which the halogen atom has an atomic number of at least 17 and the tert-alkyl group is a tert-alkyl group of from 4 to 7 carbon atoms or a tert-cycloalkyl group of from 7 to 9 carbon atoms, is contacted in solution with a butylenebis mangesium halide in which the halogen atoms have an atomic number of at least 17 and adding a proton donor to the reaction product thus produced.

10. A process for the production of a 1-tert-alkyl spiro[2,5]alkanecarboxylate in which process a tert-alkyl 1-hydrogen-2-halocyclopropanecarboxylate in which the halogen atom has an atomic number of at least 17 and the tert-alkyl group is a tert-alkyl group of from 4 to 7 carbon atoms or a tert- cycloalky group of from 7 to 9 carbon atoms, is contacted in solution with a pentylenebis magnesium halide in which the halogen atoms have an atomic number of at least 17 and adding a proton donor to the reaction product thus produced.

* * * * *